United States Patent
Yodfat et al.

(10) Patent No.: US 8,088,098 B2
(45) Date of Patent: Jan. 3, 2012

(54) TAILORED BASAL INSULIN DELIVERY SYSTEM AND METHOD

(75) Inventors: Ofer Yodfat, Maccabim-Reut (IL); Gali Shapira, Haifa (IL); Iddo Gescheit, Tel-Aviv (IL)

(73) Assignee: Medingo, Ltd., Yoqneam Illit (IL)

( * ) Notice: Subject to any disclaimer, the term of this patent is extended or adjusted under 35 U.S.C. 154(b) by 326 days.

(21) Appl. No.: 12/145,754

(22) Filed: Jun. 25, 2008

(65) Prior Publication Data
US 2008/0319384 A1    Dec. 25, 2008

Related U.S. Application Data

(60) Provisional application No. 60/937,157, filed on Jun. 25, 2007.

(51) Int. Cl.
*A61M 31/00* (2006.01)

(52) U.S. Cl. .......... 604/67

(58) Field of Classification Search .......... 604/131, 604/151, 65, 66, 67, 134, 890.1
See application file for complete search history.

(56) References Cited

U.S. PATENT DOCUMENTS

| | | | |
|---|---|---|---|
| 6,558,351 B1 * | 5/2003 | Steil et al. | 604/131 |
| 2003/0060753 A1 | 3/2003 | Starkweather et al. | 604/66 |
| 2003/0060765 A1 * | 3/2003 | Campbell et al. | 604/131 |
| 2003/0114836 A1 | 6/2003 | Estes et al. | 604/890.1 |
| 2006/0031094 A1 | 2/2006 | Cohen et al. | 705/2 |

FOREIGN PATENT DOCUMENTS

| | | |
|---|---|---|
| WO | WO 2005/113036 A1 | 12/2005 |
| WO | WO 2007/000427 A1 | 1/2007 |

OTHER PUBLICATIONS

International Search Report for PCT/IL2008/000863, mailed Sep. 24, 2008.
Scheiner, et al., "Characteristics of basal insulin requirements by age and gender in Type-1 diabetes patients using insulin pump therapy", *Diabetes Research and Clinical Practice*, 69: 14-21 (2005).
Danne et al., "Current practice of insulin pump therapy in children and adolescents—the Hannover recipe", *Pediatric Diabetes*, 7(Suppl. 4):25-31 (2006).
DCCT Trial Research Group, "The Effect of Intensive Treatment of Diabetes on the Development and Progression of Long-Term Complications in Insulin-Dependent Diabetes Mellitus", *N. Engl. J. Med.*, 329:977-986 (1993).

(Continued)

*Primary Examiner* — Christopher D Koharski
(74) *Attorney, Agent, or Firm* — Mintz Levin Cohn Ferris Glovsky and Popeo, P.C.

(57) ABSTRACT

Disclosed is a system to deliver insulin to a user's body. The system includes a dispensing unit to deliver the insulin to the body, and a control mechanism to control delivery of basal insulin according to a predetermined basal infusion pattern, the basal infusion pattern selected from a plurality of predetermined basal infusion patterns. In some embodiments, selection of the basal infusion pattern may be based on one or more personal characteristics of the user.

39 Claims, 10 Drawing Sheets

OTHER PUBLICATIONS

DCCT/EDIC Study Research Group, "Intensive Diabetes Treatment and Cardiovascular Disease in Patients with Type 1 Diabetes", *N. Engl. J. Med.*, 353(25):2643-2653 (2005).

Holterhus et al., "Classification of Distinct Baseline Insulin Infusion Patterns in Children and Adolescents With Type 1 Diabetes on Continuous Subcutaneous Insulin Infusion Therapy", *Diabetes Care*, 30:568-573 (2007).

Schaller et al., "On-line adaptive algorithm with glucose prediction capacity for subcutaneous closed loop control of glucose: evaluation under fasting conditions in patients with Type 1 diabetes", *Diabetic Med.*, 23:90-93 (2006).

Sturis et al., "24-Hour Glucose Profiles during Continuous or Oscillatory Insulin Infusion. Demonstration of the Functional Significance of Ultradian Insulin Oscillations", *J. Clin. Invest.*, 95:1464-1471 (1995).

UKPDS Group, "Intensive blood-glucose control with sulphonylureas or insulin compared with conventional treatment and risk of complications in patients with type 2 diabetes (UKPDS 33)", *Lancet*, 352:837-853 (1998).

UKPDS Group, "Tight blood pressure control and risk of macrovascular and microvascular complications in type 2 diabetes: UKPDS 38", *BMJ*, 317(7160):703-713 (1998).

* cited by examiner

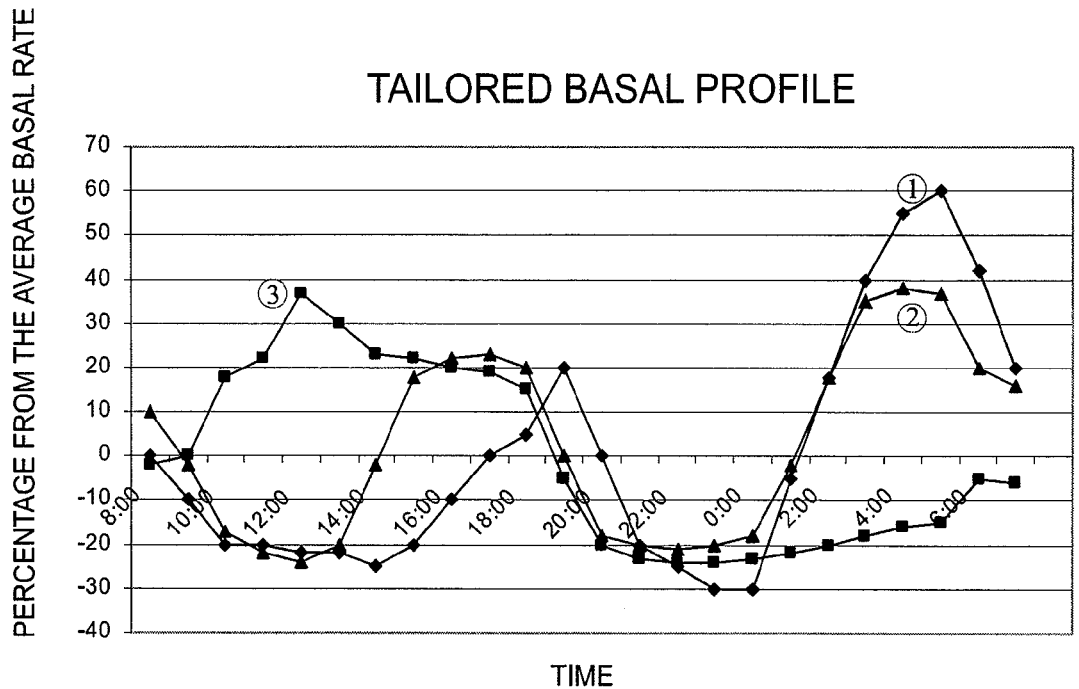

FIG. 2

| CATEGORY | PROPRIETARY NAME | ONSET | PEAK CONCENTRATION (h) | DURATION OF ACTION (h) EFFECTIVE | DURATION OF ACTION (h) MAXIMUM | DESCRIPTION |
|---|---|---|---|---|---|---|
| RAPID ACTING | LISPRO | <0.25 | 0.5-1.5 | 3-4 | 4-6 | INSULIN ANALOG |
| RAPID ACTING | ASPART | 0.17-0.33 | 0.67-0.83 | 1-3 | 3-5 | INSULIN ANALOG |
| LONG ACTING | GLARGINE | 2 | NONE | 24 | 24 | INSULIN ANALOG |
| SHORT ACTING | REGULAR | 0.5-1.0 | 2-3 | 3-6 | 6-8 | INSULIN |
| INTERMEDIATE ACTING | NPH | 2-4 | 6-10 | 10-16 | 14-18 | INSULIN |
| INTERMEDIATE ACTING | LENTE | 3-4 | 6-12 | 12-18 | 16-20 | INSULIN – ZINC (SUSPENSION) |
| LONG ACTING | ULTRALENTE | 6-10 | 10-16 | 18-20 | 20-24 | INSULIN – ZINC (SUSPENSION - EXTENDED) |

FIG. 3a

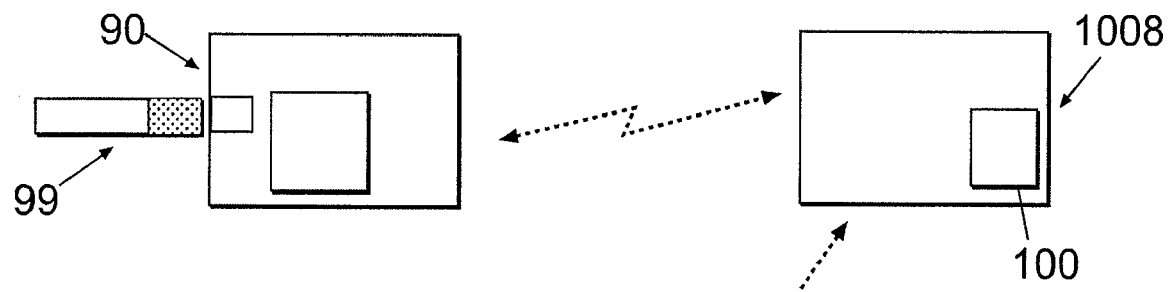
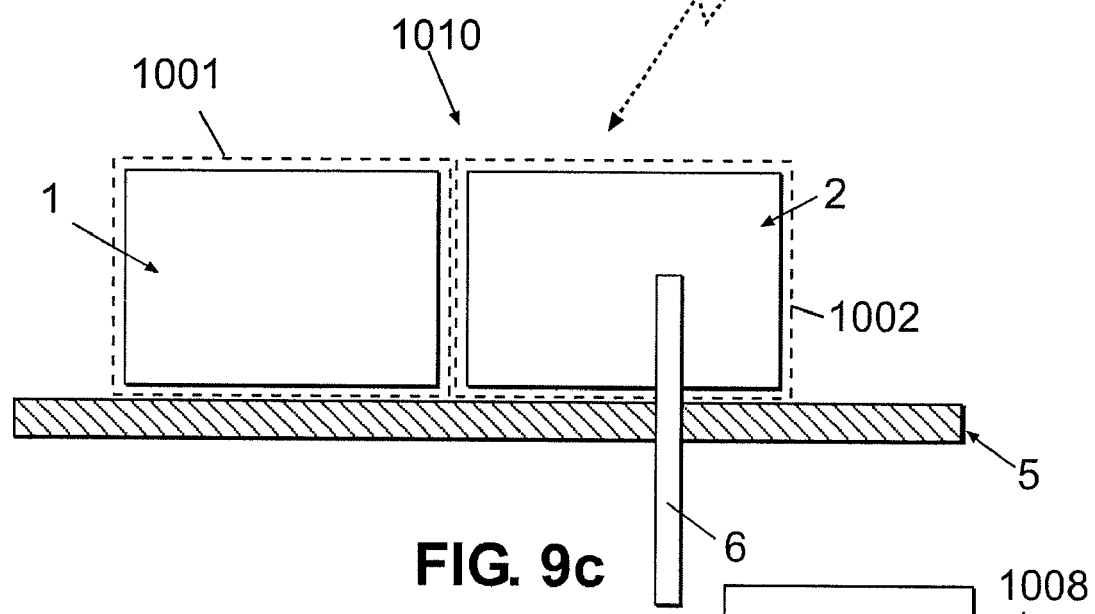
FIG. 9c
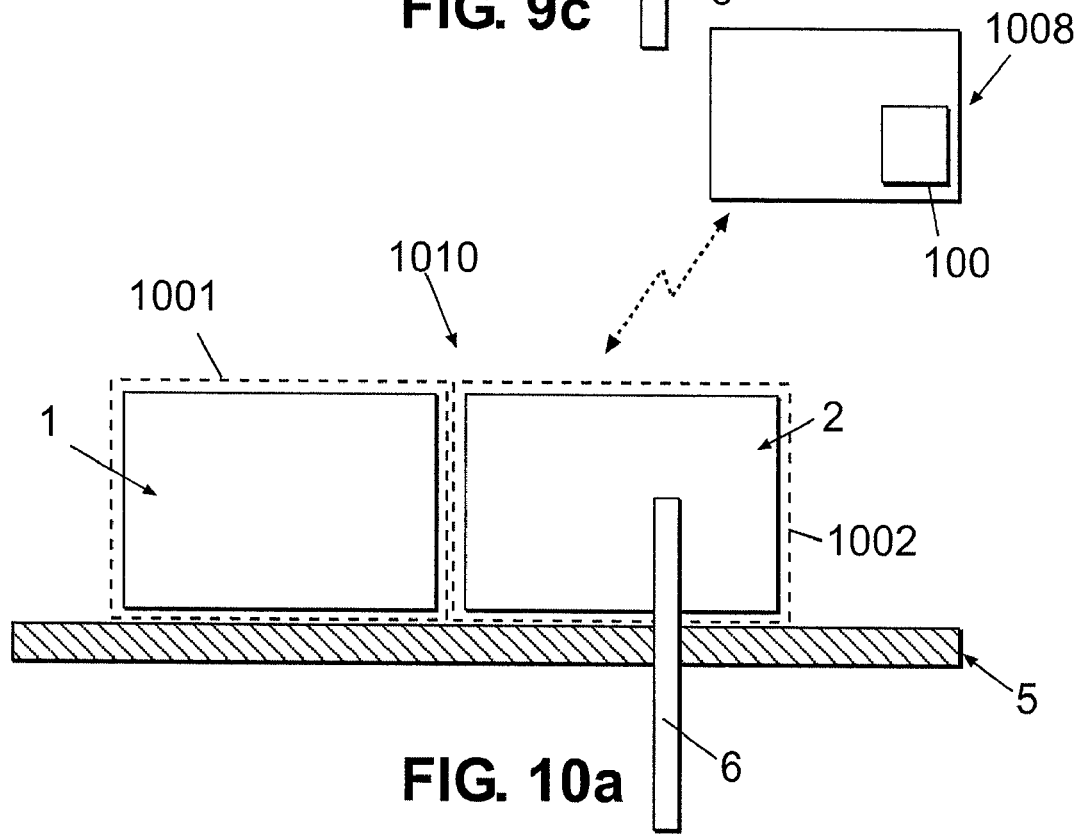
FIG. 10a

TAILORED BASAL INSULIN DELIVERY SYSTEM AND METHOD

CROSS-REFERENCE TO RELATED APPLICATIONS

This application claims priority to provisional U.S. application Ser. No. 60/937,157 entitled "TAILORED BASAL INSULIN DELIVERY SYSTEM AND METHOD", and filed Jun. 25, 2007, the content of which is hereby incorporated by reference in its entirety.

FIELD OF THE INVENTION

Embodiments of the present disclosure relate to medical devices, and more particularly to devices that administers medication into the body of a patient and/or sense analyte levels in a bodily fluid. Even more particularly, the present disclosure is related to a device and a method for delivery of basal insulin (or other therapeutic fluid) doses by a pump. In some embodiments, an insulin pump assembly is provided that includes a sensor for continuous monitoring of glucose levels. The pump may be configured to deliver basal insulin doses according to a pattern or distribution that is tailored to a patient's needs.

BACKGROUND

Diabetes and Glycemic Control

Diabetes mellitus is a disease of major global importance, increasing in frequency at almost epidemic rates, such that the worldwide prevalence as of 2006 was 170 million people and has been predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the patient and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery accordingly is of utmost importance.

Insulin pumps deliver rapid acting insulin 24 hours a day through a catheter placed under the skin. The total daily insulin dose is divided into basal and bolus doses.

Insulin bolus doses are delivered before or after meals to counteract carbohydrates loads or during episodes of high blood sugar levels.

Basal insulin is delivered continuously over 24 hours to maintain blood glucose levels in range between meals and overnight. The basal rate regulates the food-independent insulin requirement, and is predominantly dependent on hepatic gluconeogenesis, physical activity, sleep-awake circadian cycle, etc.

Generally, available pumps offer the user the ability to set a variety of basal profiles (e.g., 4-8 different profiles). The user selects a profile or profiles that best match his/her basal insulin needs. Some pumps enable the user to program a basal profile in hourly intervals, according to the user's specific daily routine and circadian basal insulin needs. Some pumps also have a temporary basal rate apparatus that is useful to manage BG levels during unusual short-term activities or conditions (e.g. unplanned physical activity).

Referring to FIG. 1, a graph of an exemplary basal pattern used, for example, with currently marketed insulin pumps is shown. The basal pattern is a 24 hour sequence of basal rates a patient is supposed to receive such that the patient is administered insulin at all times. The basal rate is generally measured in units per hour and may be changed in 30 minute intervals. However, as shown in the example, in some embodiments, the patterns used are typically divided into 3-6 segments, each segment specifying a single rate. The depicted pattern in the example of FIG. 1 provides higher insulin dosages in the evening and early morning, in conformity with the relative insulin resistance of the user during those hours.

In some embodiments, a patient may have set his/her pump on this pattern to determine through a process of trial and error an insulin infusion pattern that substantially achieves euglycemia. Such a trial-and-error approach may involve numerous hyperglycemic and hyperglycemic events.

Some studies have shown that patient age has been associated with use of different basal insulin infusion distributions. For example, in adolescents and young adults, decreased insulin sensitivity is seen, particularly in the early morning (dawn phenomenon) and to a lesser extent, in the late afternoon (dusk phenomenon). This leads to a typical two-waved basal rate profile (referred to as "dawn-dusk" pattern). High glucose values caused by a nocturnal hypoglycemia with a rebound effect (so called Somogyi phenomenon) is also evident, but is more common in MDI than in continuous subcutaneous insulin infusion (CSII). Results from the PedPump Study Group, Conrad et al. and Boland et al. also noted that younger children often need higher doses of basal insulin before midnight (between 21:00 hours and midnight). (Pediatric Diabetes 2006: 7 (Suppl. 4): 25-31, 2006).

SUMMARY OF THE INVENTION

Disclosed are systems, methods and apparatus to deliver insulin to a user's body. In some embodiments, a system to deliver insulin to the user's body includes a dispensing unit to deliver the insulin to the body, and a control mechanism to control delivery of basal insulin according to a predetermined basal infusion pattern, the basal infusion pattern selected from a plurality of predetermined basal infusion patterns. The selection of the basal infusion pattern may be based on one or more personal characteristics of the user.

A large study that analyzed the basal infusion rates of over 1200 type 1 DM children and adolescents pump users, recognized seven basal insulin infusion patterns (see, for example, Diabetes Care March 2007; 30, 3; 568-573). Age has been described as an important determinant of basal insulin infusion rate pattern. Additional factors, or predictors, that affect the insulin infusion rate patterns include the body-mass-index (BMI) of a patient, and bolus insulin requirements. Sex, duration of diabetes, and metabolic control were not found to be significant predictors of basal insulin patterns. Most of the pubertal and post-pubertal participants' insulin requirements conformed to the two-waved (dawn-dusk) pattern. Decreasing age seemed to shift the programmed dawn peak basal rate back in time, leading to a fusion of the dusk and dawn peaks (monophasic pattern).

The above-mentioned factors influence the circadian variation of insulin sensitivity, and thus insulin requirement, and are therefore crucial for insulin pump users, particularly children.

It has been documented that frequent insulin infusion variability appears to promote glucose utilization more efficiently in comparison with a constant infusion (J. Clin Invest 1995: 95:1464-1471). A study conducted by Hovorka (Diabetic Medicine 23, 90-93, 2006), has modeled optimal basal infusion rates that vary each 15 minutes. Currently used basal profiles generally enable hourly variations in the infusion rates, and may therefore not be sufficient to enable optimal glycemic control between meals.

In some embodiments of the present disclosure, a device to deliver basal insulin and a method to enable appropriate basal delivery according to user's diurnal insulin requirement to achieve better glycemic control are provided. Basal delivery based on a user's diurnal insulin requirement may be referred to as "tailored basal insulin profile".

In some embodiments, a device that delivers basal insulin and a method that enable setting of tailored basal insulin pattern or patterns over time to achieve improved glycemic control are provided.

In some embodiments, a device that continuously delivers basal insulin and a method to set a tailored basal insulin profile are provided. The device may be a portable insulin pump, skin securable insulin dispenser or any other dispensing mechanism for periodical and/or continuous insulin delivery (such delivery methods referred to as continuous subcutaneous insulin infusion, or CSII).

In some embodiments, an insulin dispensing device and a method to determine the suitability of the tailored basal insulin pattern and update the pattern if needed so as to improve glycemic control are provided.

In some embodiments, a device that dispenses basal insulin and a method to trace and update a tailored basal insulin profile and to provide the diabetes patient with recommendation of treatment adjustments are disclosed.

In some embodiments, a device that dispenses basal insulin and that continuously monitors glucose level and a method to tailor basal insulin profile are provided.

In some embodiments, a device that dispenses basal insulin doses according to the tailored basal insulin profile is provided.

In some embodiments, a device that continuously dispenses basal insulin and monitors glucose levels and can dispense insulin according to glucose readings, and a method to incorporate a tailored basal insulin profile for use with such a device, are provided.

In some embodiments, a device that is miniature, discreet, economical for the users and cost effective, and a method to incorporate a tailored basal insulin profile to facilitate operation of such a device, are provided.

In some embodiments, a device configured as a miniature patch that can be secured to the skin and can periodically and/or continuously dispense insulin, and a method to incorporate a tailored basal insulin profile to facilitate control and operation of such a device are provided.

In some embodiments, a device that comprises an insulin infusion patch unit that can be remotely controlled, and a method to incorporate a tailored basal insulin profile to facilitate operation of such a device are provided. In some embodiments, the tailored basal insulin profile is stored in a remote unit that is used to facilitate control of the device.

In some embodiments, a device comprising a miniature skin securable patch that can continuously dispense insulin and monitor body glucose concentration levels, and a method to incorporate a tailored basal insulin profile to facilitate operation of such a device are provided.

In some embodiments, a device that contains a semi closed loop system that monitors glucose levels and dispenses insulin according to the sensed glucose levels, and a method to incorporate a tailored basal insulin profile to facilitate operations of such a device are provided.

In some embodiments, a device that includes a semi closed loop system, and which is miniature, discreet, economical for the users and cost effective, and a method to incorporate a tailored basal insulin profile to facilitate operations of such a device are provided.

Embodiments of the present disclosure include a pump that periodically/continuously dispenses basal insulin, and which can be coupled to a continuous glucose monitor, and a method to tailor basal insulin patterns to user's basal insulin diurnal needs are provided.

In some embodiments, a system and method to deliver basal insulin to enable setting of tailored basal insulin pattern or patterns over time and achievement of glycemic control are provided.

In some embodiments, a system and method to continuously and/or periodically deliver basal insulin according to an established, tailored basal insulin profile are disclosed. The system may include a portable insulin pump, skin securable insulin dispenser or any other module or device to enable continuous (or periodic) insulin delivery to thus implement continuous subcutaneous insulin infusion (CSII).

In some embodiments, a system and method are disclosed to determine the suitability of the tailored basal insulin pattern and adjust (e.g., update) the pattern, if needed, to thus improve glycemic control.

In some embodiments, a system and method disclosed to dispense basal insulin are disclosed. The system is configured to determine the efficacy of a tailored basal insulin profile, and to provide a diabetes patient with recommendations regarding treatment adjustments.

In some embodiments, a system and method to dispense basal insulin are disclosed. The system is configured to continuously (or periodically, with any other suitable frequency) monitor glucose level and tailor a basal insulin profile.

In some embodiments, a system and method in which an insulin infusion patch unit is remotely controlled and in which the infusion patch is configured to dispense insulin according to a tailored profile are disclosed. At least a portion of the mechanism (or apparatus) responsible for tailoring the basal insulin profile may be located in the remote unit.

In some embodiments, a system and method in which a miniature skin adherable patch dispenses (e.g., continuously or periodically dispenses) insulin according to a tailored basal insulin profile are disclosed. The system may also include a sensing device to monitor body glucose concentration levels.

In some embodiments, a system and method are disclosed in which a semi-closed loop system monitors glucose levels and dispenses insulin according to the sensed glucose levels, and additionally incorporates a tailored basal insulin profile to facilitate control and operation of insulin dispensation.

The systems provided with tailored basal profiles in accordance with some embodiments of the present disclosure may include a semi-closed loop system, which is miniature, discreet, economical for the users and cost effective for the payer.

It is an object of some of the embodiments of the present disclosure to provide a system and/or device that continuously (or periodically, e.g., semi-continuously) monitors body glucose levels and concomitantly delivers insulin into the body based, at least in part, on a basal insulin pattern tailored for the user.

It is an object of some of the embodiments of the present disclosure to provide a system comprising a miniature skin securable patch that can continuously or periodically dispense insulin according to a basal insulin profile tailored for the user.

It is an object of some of the embodiments of the present disclosure to provide a system comprising a miniature skin securable patch that can continuously or periodically dispense insulin according to a basal insulin profile tailored for the user, and that can further monitor body glucose levels.

It is an object of some of the embodiments of the present disclosure to provide a closed or semi-closed loop system to monitor glucose levels and dispense insulin according to the sensed glucose levels, and also to tailor an initial basal insulin profile for the user. Such systems may be implemented as miniature single devices that are discreet, economical and cost-effective.

It is an object of some of the embodiments of the present disclosure to provide a device that includes an insulin infusion patch unit comprising a disposable part and a reusable part. The reusable part may include the relatively expensive components while the disposable part may include the relatively inexpensive components, thus providing a cost-effective therapeutic fluid (e.g., insulin) dispensing device for the user. The device may implement a procedure for tailoring a basal insulin profile for the user.

It is an object of some of the embodiments of the present disclosure to provide a device that comprises an insulin infusion and a continuous glucose monitor patch unit comprising a disposable part and a reusable part. The reusable part may contain the relatively expensive components and the disposable part may contain the relatively inexpensive components, thus providing a cost-effective device for the user. The device may implement a procedure for tailoring a basal insulin profile for the user.

It is an object of some of the embodiments of the present disclosure to provide a device that comprises an insulin infusion patch unit that can be remotely controlled and a method for tailoring a basal insulin profile for the user.

It is an object of some of the embodiments of the present disclosure to provide a device that comprises insulin infusion and continuous glucose monitor patch unit that can be remotely controlled, and a method for tailoring a basal insulin profile for the user.

In some embodiment, several predetermined basal insulin infusion patterns are available. A controller (or the user) may initially select a pattern that most closely mimics his/her own diurnal insulin sensitivity (i.e., the amount of blood glucose lowered by one unit of insulin). Selection of the pattern from the predetermined available patterns may be based on one or more personal characteristics of the user.

In some embodiments, the tailored basal insulin pattern is based on one or more of the following personal characteristics (parameters) of the particular user: age, body-mass-index (BMI) and/or the bolus insulin requirements. Additional characteristics such as, for example, sex, duration of diabetes, metabolic control, physical activity, sleep pattern and sleep duration (hormones that are antiregulatory to insulin are secreted in sleep, e.g. growth hormone that controls IGF-1 production), hemoglobin A1c values, age at manifestation of DM, prandial insulin per kilogram per day, and total insulin per kilogram per day may also be considered when selecting the initial basal pattern.

In some embodiments, determination (e.g., selection) of the tailored basal insulin pattern may be based on age alone.

In some embodiments, the tailored basal insulin patterns include patterns of basal insulin infusion rate changes rather than as absolute dosages per time segment (e.g., hourly).

In some embodiments, the user may input his/her total daily dose (TDD) and the device may distribute the TDD according to a suitable basal insulin pattern (e.g., as determined based on computer program instructions programmed into the device).

In some embodiments, if an insulin preparation with different pharmakokonetics from rapid acting insulin is used, the tailored basal pattern may be adjusted, e.g., shifted in time to fit the different pharmacokinetics.

In some embodiments, if normal insulin is used, as opposed to rapid acting insulin (e.g., NovoRapid, Humalog), the basal insulin infusion rate patterns may be shifted forward a predefined unit of time (e.g., 1 hour) in order to agree with the user's specific basal insulin needs.

In some embodiments, children and adolescents (e.g., up to age 18) will be assigned one of several (e.g., seven) basal insulin infusion rate patterns, based mainly on their age.

Users in the ages of 12.5-17.3 (for example) may be assigned a biphasic "dawn-dusk" pattern, with a higher insulin peak in at a point of the pattern corresponding to the early morning rather than at a point corresponding to the late afternoon. Decreasing age may change the initially set basal pattern so that the dawn peak of the "dawn-dusk" pattern is shifted back in time, leading to a virtual fusion of the dawn and dusk peaks. Users in the ages of 4.5-11 may be assigned a monophasic basal insulin infusion rate with a broad insulin peak at a point of the pattern corresponding approximately to 9-10 p.m.

In some embodiments, the patient will be able to temporarily change his basal profile in magnitude but not in relative distribution (e.g., general behavior of the pattern), thus adjusting to special situations such as illness and fever that requires more insulin, initiation of treatment with drugs that raise the insulin need (e.g. cortisone), or prolonged physical activity that reduce the insulin needs.

In some embodiments, the tailored basal insulin profile may be changed by a physician or by a user.

In some embodiments, the new tailored basal insulin profile is automatically adjusted.

In some embodiments, the method for tailoring basal insulin can be implemented in an insulin infusion device.

In some embodiments, the method for tailoring basal insulin profile can be implemented in a glucose monitoring device.

In some embodiments, the method for tailoring a basal insulin profile can be implemented in a device which can deliver insulin and monitor glucose.

In some embodiments, the method for tailoring a basal insulin profile is implemented in an insulin infusion device comprising an insulin dispensing patch unit and a remote control unit. A glucose sensing apparatus (e.g. glucometer) may be integrated in the remote control unit. In some embodiments, the patch unit may be composed of two parts, namely, a reusable part that includes electronic, driving, and pumping elements, and a disposable part that includes, for example, an insulin reservoir. The glucose sensing apparatus (e.g., glucometer) may alternatively be integrated in the reusable part of the patch unit of the device.

In some embodiments, the method for tailoring basal insulin profile is implemented in the remote control unit of the insulin infusion device. Alternatively, the method for tailoring basal insulin profile could be implemented in the reusable part of the patch unit of the device.

In some embodiments, the method for tailoring basal insulin profile is implemented in the patch unit that continuously monitors body glucose levels and can concomitantly deliver insulin into the body. The patch unit may include a reusable part and a disposable part.

In some embodiments, the method for tailoring a basal insulin profile is implemented in the remote control unit of the device. Alternatively, the method could be implemented in the reusable part of patch unit of the device. Alternatively, the method could be implemented in both the reusable part of the patch unit of the device and the remote control unit of the device.

In some embodiments, if insulin requirements are very low (e.g., neonates may need basal dosage of 0.1 IU/h), the device may generate a recommendation to perform dilution of the insulin preparation. Generally, rapid-acting analogs are available in 100 IU (100 IU per ml). If the basal rate per hour is very low (e.g., 0.1 IU per hour) this low hourly fluid throughput may lead to a faster catheter obstruction compared with more dilute insulin and a higher fluid throughput. To avoid this problem, an insulin dilution may be prepared using an insulin-free medium.

In some embodiments, the dispensing device may comprise an insulin free medium and may perform automatic insulin dilution. The volume dispensed will be in based on the dilution.

In one aspect, a system to deliver insulin to a user's body is disclosed. The system includes a dispensing unit to deliver the insulin to the body, and a control mechanism to control delivery of basal insulin according to a predetermined basal infusion pattern, the basal infusion pattern selected from a plurality of predetermined basal infusion patterns.

Embodiments of the system may include one or more of the following features.

Selection of the basal infusion pattern may be based on one or more personal characteristics of the user.

The dispensing unit may include a reservoir to hold the insulin, a cannula having an end for placement within the user's body, and a pump to deliver the insulin from the reservoir to the cannula.

The control mechanism to control delivery of the basal insulin may include a processor configured to control delivery of the basal insulin by the pump according to the selected basal infusion pattern, the basal infusion pattern including a pre-defined sequence of basal infusion rate changes. The rate changes of the pre-defined sequence may be defined at intervals of one hour or shorter. The pre-defined sequence may include a pre-defined sequence of deviations from an average basal infusion rate.

The control mechanism may be further configured to time shift the basal infusion pattern based on the type of basal insulin to be held within a reservoir of the dispensing unit.

The system may further include a user input interface in communication with the control mechanism. The control mechanism may be further configured to adjust the magnitude of the basal insulin delivered without disrupting the sequence of basal infusion rate changes defined by the basal infusion pattern in response to user input, entered through the user input interface, to increase or decrease the dosage of insulin delivered by the dispensing unit.

The control mechanism may include a basal infusion rate pattern mechanism to determine the basal infusion pattern based on one or more personal characteristics of the user. The basal infusion pattern mechanism may be configured to determine the basal infusion pattern based on the one or more personal characteristics of the user, including one or more of, for example, age, body-mass index (BMI), bolus insulin requirements, sex, duration of diabetes, metabolic control, physical activity, sleep pattern, sleep duration, hemoglobin A1c values, age at manifestation of Diabetes Mellitus (DM), pyramidal insulin per kilogram, prandial insulin per day, total insulin per kilogram and/or total insulin per day. The basal infusion pattern mechanism configured to determine the basal infusion pattern may be configured to select a basal infusion pattern from a plurality of pre-defined patterns based on the one or more personal characteristics of the user.

The basal infusion pattern may be selected based on the user's age.

The selected basal infusion pattern may be determined based on physiological diurnal needs of basal insulin.

The plurality of predetermined basal infusion patterns may include a biphasic pattern having a peak at a point of the pattern corresponding to a period of early morning and a peak at another point of the pattern corresponding to a period of late afternoon.

The plurality of predetermined basal infusion patterns may include a monophonic pattern having a broad insulin peak at a point of the pattern corresponding to a period of around noon.

The system may further be configured to collect data regarding efficacy of the selected basal infusion pattern, and adjust the selected basal infusion pattern based on the collected data.

The control mechanism to control delivery of the basal insulin according to the basal infusion pattern may be configured to determine the basal infusion pattern based on the one or more personal characteristics of the user, and perform an evaluation of suitability of the determined basal infusion pattern based on glycemic status of the user. The control mechanism configured to perform the evaluation of the suitability of the basal infusion pattern may be configured to evaluate the suitability of the basal pattern based on data representative of deviations of a user's glucose level from a target zone. The control mechanism configured to perform the evaluation of the suitability of the basal infusion pattern may be configured to evaluate the suitability of the basal pattern based on data representative of a user's hemoglobin A1C levels.

The control mechanism may be further configured to adjust the selected basal infusion pattern based on the evaluation indicating lack of suitability of the determined basal infusion pattern.

The control mechanism may be further configured to determine another basal infusion pattern based on the evaluation indicating lack of suitability of the basal infusion pattern. The control mechanism configured to determine the other basal infusion pattern based on the evaluation indicating lack of suitability may be configured to select the other basal infusion pattern from the plurality of basal infusion patterns based on the evaluation indicating lack of suitability.

The system may further include a remote control housed remotely from the dispensing unit.

The system may further include a glucometer to measure blood glucose levels of the user.

The control mechanism to control delivery of the basal insulin according to the selected basal infusion pattern may further be configured to control delivery of the basal insulin based, at least in part, on the measured blood glucose levels of the user.

The system may further include a cradle unit securable to the body of the user, the cradle unit configured to receive at least the dispensing unit.

In another aspect, a method for delivering basal insulin to a body of a user is disclosed. The method includes determining a predetermined basal infusion pattern from a plurality of predetermined basal infusion patterns, and delivering to the body of the user insulin based on the determined basal infusion pattern.

Embodiments of the method may include any of the features described above in relation to the system, as well as any one of the following features.

Determining the predetermined basal infusion pattern may include selecting the basal infusion pattern for the user from a plurality of pre-determined basal infusion patterns based on one or more personal characteristics of the user.

In a further aspect, an apparatus to deliver doses of basal insulin to a body of a user is disclosed. The apparatus includes a user interface to receive input regarding at least one characteristic of the user, and a tailored basal insulin profile mechanism to select a basal infusion pattern for the user from a plurality of basal insulin infusion patterns based, at least in part, on the received input.

Embodiments of the apparatus may include any of the features described above in relation to any one of the system and method.

It is to be noted that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

Embodiments of the present disclosure, including the various objects and advantages thereof, are described in reference to the following illustrative drawings.

FIG. 2 is a graph of exemplary basal insulin distribution rates tailored based on patients' age.

FIGS. 3a and 3b are a table and graph, respectively, of exemplary tailored basal patterns adjusted to different insulin preparations.

FIGS. 9a, 9b and 9c are schematic diagrams of an exemplary insulin infusion device that includes a blood glucose monitor in three different locations to provide blood glucose (BG) readings for a tailored basal insulin profile mechanism.

FIGS. 10a and 10b are schematic diagrams of two exemplary embodiments of insulin infusion devices that include tailored basal insulin profile mechanism placed in different locations.

DETAILED DESCRIPTION

Disclosed is a system to deliver insulin to a user's body. The system includes a dispensing unit to deliver the insulin to the body, and a control mechanism to control delivery of basal insulin according to a basal infusion pattern tailored to the user. As will be described in greater details below, the tailored basal infusion pattern may be determined based on one or more personal characteristics of the user.

Referring to FIG. 2, graphs of exemplary of three initial basal insulin infusion rate distributions (i.e. patterns) that may be used by devices described herein. Upon initially starting operation of an infusion device such as the infusion devices described herein, a user (e.g., a patient) is initially assigned a basal insulin infusion pattern that is most likely to conform with that patient's basal insulin distributional needs. This initial assignment may be based, at least in part, on known personal characteristics of the patient, e.g., the user's age. Other personal characteristic may be used to determine the initial basal insulin distribution profile to use. In some embodiments, determination of the initial profile to use is performed by selecting one of a plurality of pre-defined profiles stored in a storage unit of the insulin infusion device.

Pattern 1 (marked using diamond shaped cursors), represents a biphasic "dawn-dusk" pattern having a higher insulin peak in the early morning than in the late afternoon. Such a pattern may be selected as the initial pattern assigned to a user in circumstances in which the user is in his/her late puberty or post-puberty age (e.g., 15-17 years of age). Pattern 2 (marked using triangular cursors) represents another biphasic "dawn-dusk" pattern having an insulin peak in the early morning that is lower than that used, for example, in pattern 1, and also having an earlier afternoon peak. Pattern 2 may be suitable for slightly younger users (e.g., in the ages of 12-14 years). Pattern 3 (marked using square shaped cursors) depicts a monophasic basal insulin infusion rate having a broad insulin peak at around noon. Such a pattern may be initially selected for users in their late pre-puberty stage (e.g., ages of 8-11 years). While the patterns depicted in FIG. 2 specify insulin infusion rates at one-hour intervals, in some embodiments, the basal insulin rate may be changed (specified) at more frequent intervals (e.g., 15 minute intervals).

Referring to FIG. 3a, a table representing the different properties of exemplary commercial insulin preparations is shown. Suitable insulin preparations used in performing SCII include, for example, rapid acting insulins (e.g., Lispro, Aspart). The rapid acting insulins reach their peak plasma concentrations within 0.5-1.5 hours. The regular insulin reaches its peak plasma concentrations within 2-3 hours.

Figure 1:
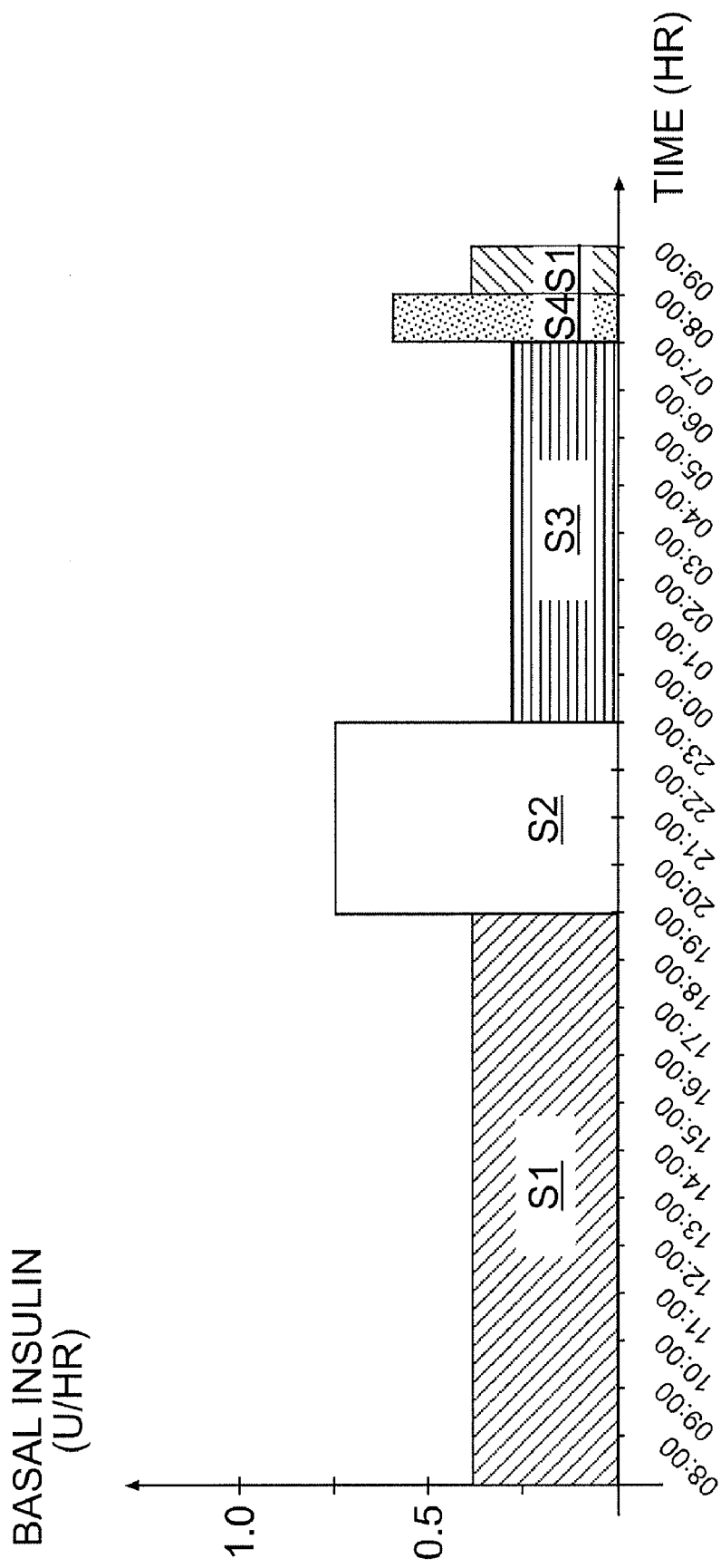
FIG. 1 is a graph of an exemplary basal insulin profile such as profiles used with currently available insulin pumps.
Figure 3B:
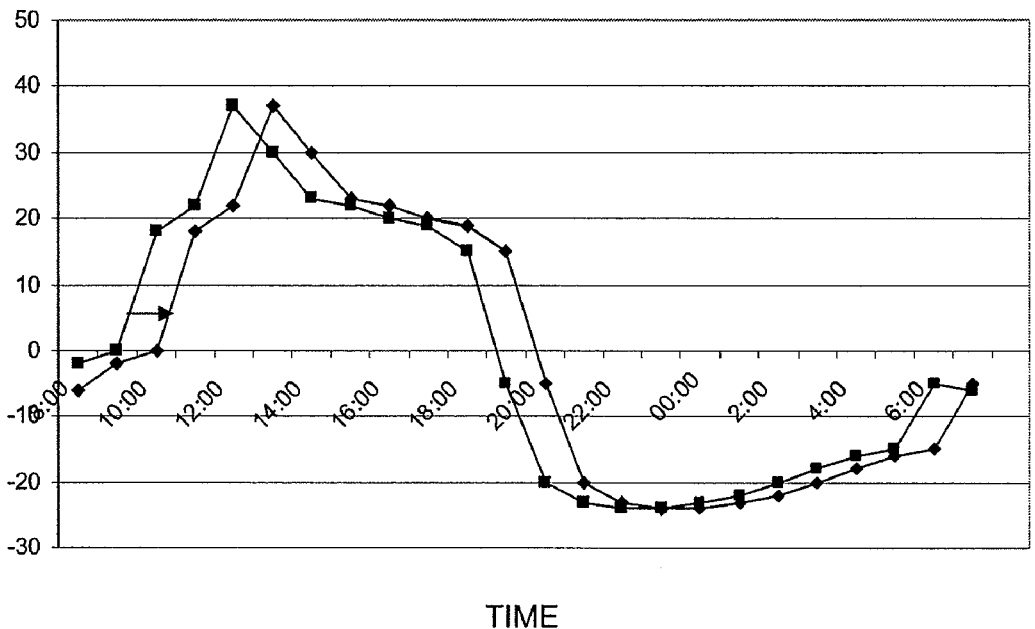

Referring to FIG. 3b, a graph of an exemplary tailored basal insulin pattern (marked with square shaped cursors) based on the use of a rapid acting insulin, is compared to a shifted basal insulin pattern (diamond shaped cursors) that is based on the use of a regular insulin. As shown, the tailored basal pattern is shifted in time, e.g., by one hour, to fit the different pharmacokinetics. Thus, in embodiments in which an insulin preparation with different pharmakokonetics and/or pharmacodynamics from those corresponding to rapid acting insulin is used, the tailored basal pattern may be shifted in time, to fit the different pharmacokinetics and/or pharmacodynamics. In some embodiments, if regular insulin is used rather than rapid acting insulin (e.g. NovoRapid, Humalog), the basal insulin infusion rate patterns may be shifted forward by one (1) hour in order to agree with the user's specific basal insulin needs.

Figure 4:
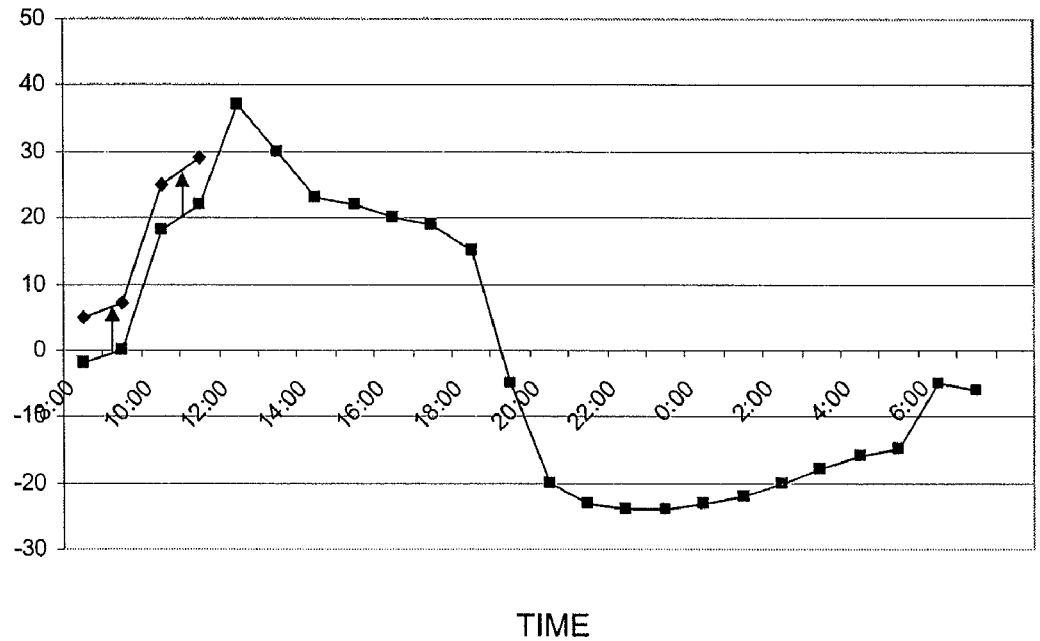
FIG. 4 is a graph of an exemplary basal pattern adjusted to make a temporary change to the magnitude of the basal insulin while maintaining the characteristics of the profile's pattern.

Referring to FIG. 4, a graph of an exemplary basal pattern adjusted to make a temporary change to the magnitude of the basal insulin, while otherwise maintaining the characteristics of the profile's pattern, is shown. Thus, in some embodiments, specific segments of an infusion pattern may be altered, temporarily or more permanently, to increase or decrease the infusion rate (e.g., the level of insulin infused into the patient's body). Such changes may be effected by the patient him/herself, or by some qualified user (e.g., a doctor, technician, etc.) to adjust the infusion pattern. In the given example, the user temporarily increased the basal insulin level from 8:00 to 12:00 (e.g., due to a skipped physical training that is in the user's daily routine, or due to a host of other possible reasons affecting the patient's insulin needs).

Figure 5:
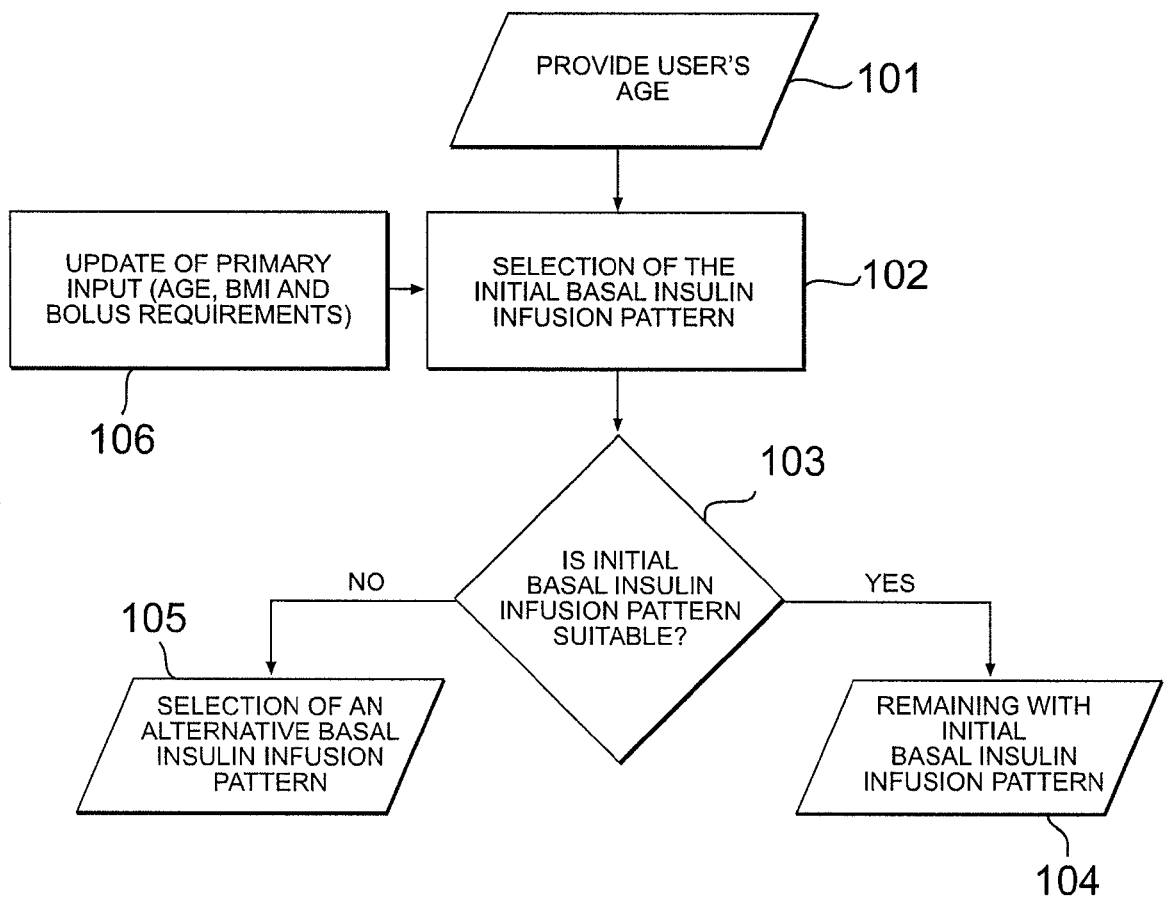
FIG. 5 is a block diagram of an exemplary of a tailored insulin infusion rate distribution procedure.

Referring to FIG. 5, a block diagram of an exemplary insulin infusion pattern selection procedure, performed, for example, by a tailored basal insulin pattern mechanism (also referred to as tailored basal insulin profile apparatus) is shown. Initially, input data required to enable determination (e.g., selection) of a suitable initial basal insulin profile from a plurality of pre-determined profiles is provided 101. In some embodiments, the input data that may be provided may include personal characteristics of the patient, including, for example, the age of the patient, the patient weight, the patient's body-mass index (BMI), etc. Once the required input is received by the apparatus, a selection of the suitable initial basal insulin infusion pattern is made 102. The selection may be performed, for example, by computing a score for each of the available pre-defined patterns representative of the suitability of that pattern for insulin infusion for the patient in view of the provided personal characteristics of the patient. Computed scores may be ranked, and the pattern corresponding to the "best" score is deemed to be the most suitable pattern, and may thus be selected for further processing. In some embodiments, having selected the initial pattern, the suitability of the selected pattern is evaluated 103. The evaluation of the selected pattern may be based, for example, on a determination of the glycemic status of the patient, thus enabling the suitability of the selected pattern to be determined. In some embodiments, the glycemic status may be determined based on periodic data (e.g., at 3-month intervals) of hemoglobin A1C levels. In some embodiments, the glycemic status may be determined based on continuous glucose measurements (CGM), based upon which the number and duration of deviations from the blood glucose (BG) target zone may be determined, i.e., the number of times the user is hypoglycemic or hyperglycemic and the time duration spent in those states.

If the initially selected basal insulin infusion pattern is determined to be suitable based on, for example, the evaluation of the glycemic status of the patient, the initially selected pattern is confirmed 104 as the pattern to be used to perform insulin infusion to the patient.

If, on the other hand, it is determined that the initially selected pattern is not suitable for the patient (e.g., based on the evaluation of the patient's glycemic status), an alternate basal insulin infusion pattern is selected 105. In some embodiments, the alternatively selected pattern may be, for example, the second most suitable pattern (in circumstances in which a pattern ranking is performed, as described in relation to the operations 102 described above), as determined based on the user's specific personal characteristics.

In some embodiments, any changes to the primary input based upon which an initial selection of suitable patterns is made (e.g., age, BMI, bolus insulin requirements) results in the updating 106 of the inputs provided to the apparatus, and the pattern selection procedure is performed again.

As noted, in some embodiments, the selection of the suitable (e.g., optimal) initial basal pattern may be based on additional primary user input such as BMI, bolus insulin requirements, sex, duration of diabetes, metabolic control, physical activity, sleep pattern and sleep duration, hemoglobin A1c values, age at manifestation of DM, prandial insulin per kilogram and day, and total insulin per kilogram and day. In some embodiments, the initial selection of the optimal basal pattern (as performed at 102) may be based on a single factor, e.g., the user's age only. In some embodiments, the operations of initially selecting a pattern from a repertoire of predefined patterns, and evaluating the suitability of the selected pattern may be consolidated into a process in which the initial selection is based, in addition to the primary personal characteristics of the patient, also on the factors that are used in the procedure of FIG. 5 to perform the evaluation of the suitability of the selected pattern. Thus, for example, in some embodiments the initial selection of the pattern from the plurality of pre-defined pattern will factor in the glycemic status of the patient.

Figure 6:
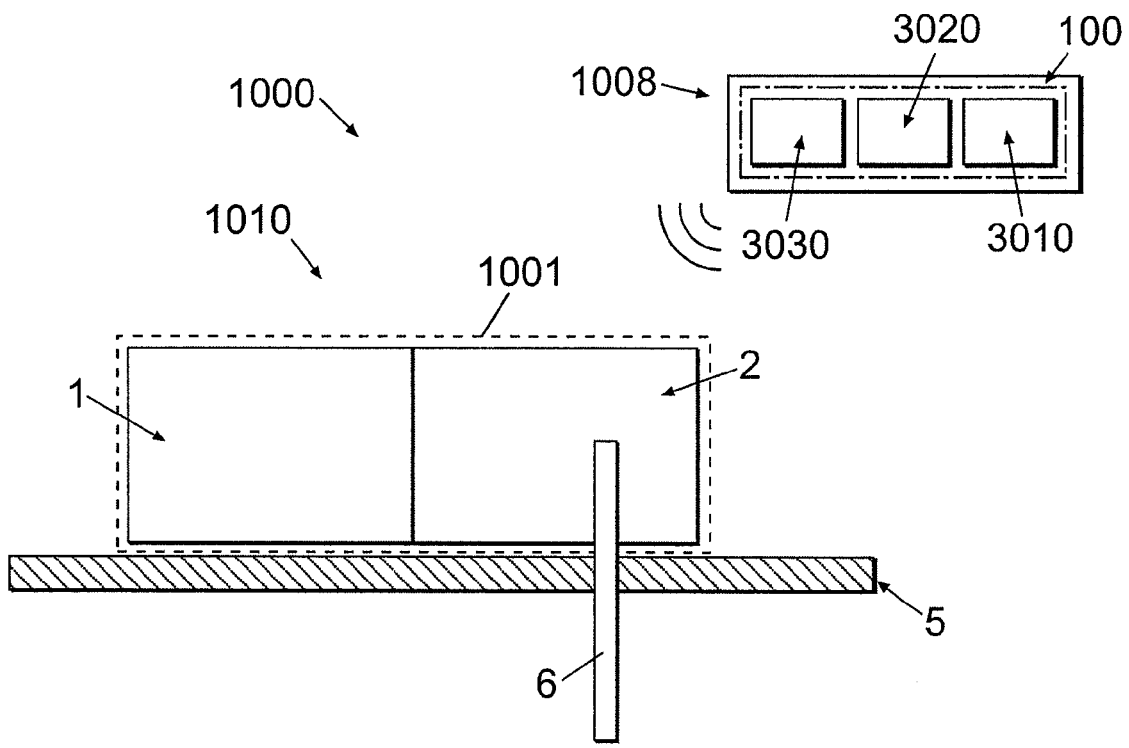
FIG. 6 is a schematic diagram of an exemplary insulin infusion device that includes an insulin dispensing unit and a remote control unit that contains a tailored basal insulin profile mechanism.

Referring to FIG. 6, a schematic diagram of an insulin infusion system 1000 is shown. The insulin infusion system includes a patch unit 1010 which can be secured to a patient's skin 5, and a remote control unit 1008 to communicate with the dispensing patch unit 1010 to enable programming of the patch unit, communication of user inputs and acquired data, etc.

In some embodiments, manual inputs may be provided through a user interface, e.g., a user interface comprising buttons, located on the patch unit. The patch unit may include a single housing 1001 to house the various modules/components of the patch unit, or, alternatively, may include two attachable parts (each having its own separate housings) such as a reusable part 1 and a disposable part 2.

As shown, the patch unit 1010 includes a cannula 6 to penetrate the skin 5 to enable delivery of insulin. The patch unit (1010) may be directly attached to the patient's skin by adhesives (not shown) or may be attached to a dedicated cradle unit (not shown) securable to a patient's skin to thus enable connection and disconnection of the patch unit.

As further shown, the remote control unit 1008 includes a tailored basal insulin profile mechanism 100 to determine the basal insulin pattern (or profile) that is used to control infusion of the insulin (or other types of therapeutic fluids) into the patient's body. In some embodiments, the insulin profile mechanism may be implemented using a processor-based device configured to execute processor instructions that cause the insulin pattern determination processes to be performed. Such implementations of the insulin profile mechanism may thus include a processor 3010, a user input interface 3020 and a user output interface, such as a display 3030. The input interface may be used to provide user input for both the tailored basal insulin profile mechanism 100 and to perform or facilitate patch unit programming.

Figure 7A:
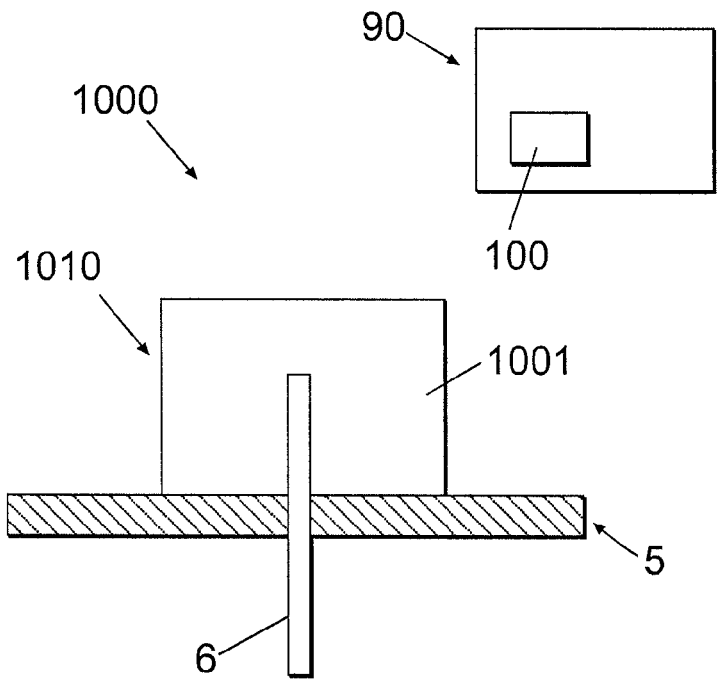
FIGS. 7a and 7b are schematic diagrams of an exemplary system comprising an insulin infusion pump, a glucose measurement device, and apparatus incorporating a tailored basal insulin profile.
Figure 7B:
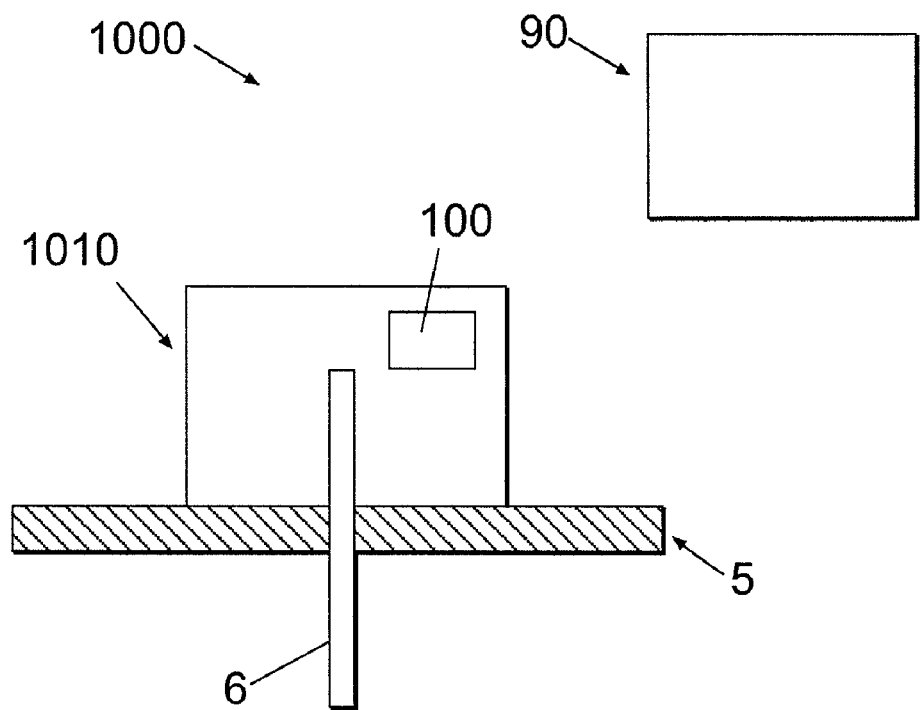

Referring to FIGS. 7a and 7b, schematic diagrams of an exemplary insulin infusion system 1000 are shown. Embodiments of the system 1000 of FIGS. 7a and 7b includes an insulin infusion pump 1010, a glucose measurement device (e.g., glucometer) 90, and a tailored basal insulin profile mechanism (e.g., apparatus) 100 to perform tailored insulin basal profile determination. The insulin infusion pump 1010 includes a cannula 6 to penetrate the skin 5 of a patient to enable delivery of insulin.

As shown in FIG. 7a, the tailored basal insulin profile mechanism 100 is installed in the glucose measurement device 90. In FIG. 7(b), on the other hand, the tailored basal insulin profile mechanism 100 is installed in the insulin infusion pump 1010. In some embodiments, the insulin infusion pump 1010 communicates with a remote control unit to enable communication of programming instructions, user inputs and data acquisition. In such embodiments, the tailored basal insulin profile mechanism may be installed in the remote control unit.

In some embodiments, the insulin infusion pump comprises a glucometer. Alternatively, the glucometer may be installed in the remote control unit of the pump or in the pump unit itself. The tailored basal insulin profile mechanism may be installed in any of the glucometer unit, pump unit, or remote control unit.

In some embodiments, the system comprises an insulin infusion pump, a continuous glucose measurement (CGM) device, and a tailored basal insulin profile mechanism. The tailored basal insulin profile mechanism may be installed in either the pump or the CGM device. In some embodiments, the insulin infusion pump comprises a continuous glucose measurement (CGM) device. The infusion pump and continuous glucose measurement (CGM) device may be disposed in the same housing and may communicate with a remote control unit. A tailored basal insulin profile mechanism may be installed in the CGM and pump unit, or in the remote control unit.

Figure 8A:
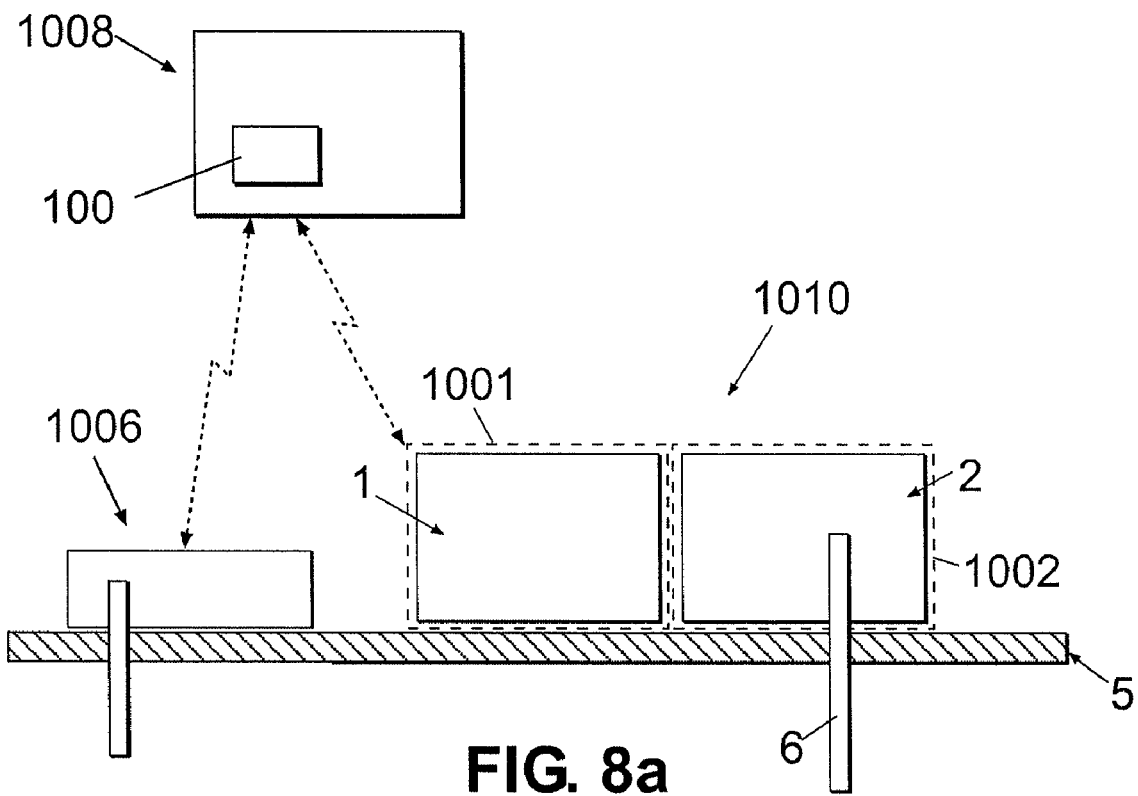
FIGS. 8a and 8b are schematic diagrams of exemplary embodiments of two insulin infusion devices that include continuous subcutaneous glucose monitors performing blood glucose readings (BG) for a tailored basal insulin profile mechanism.
Figure 8B:
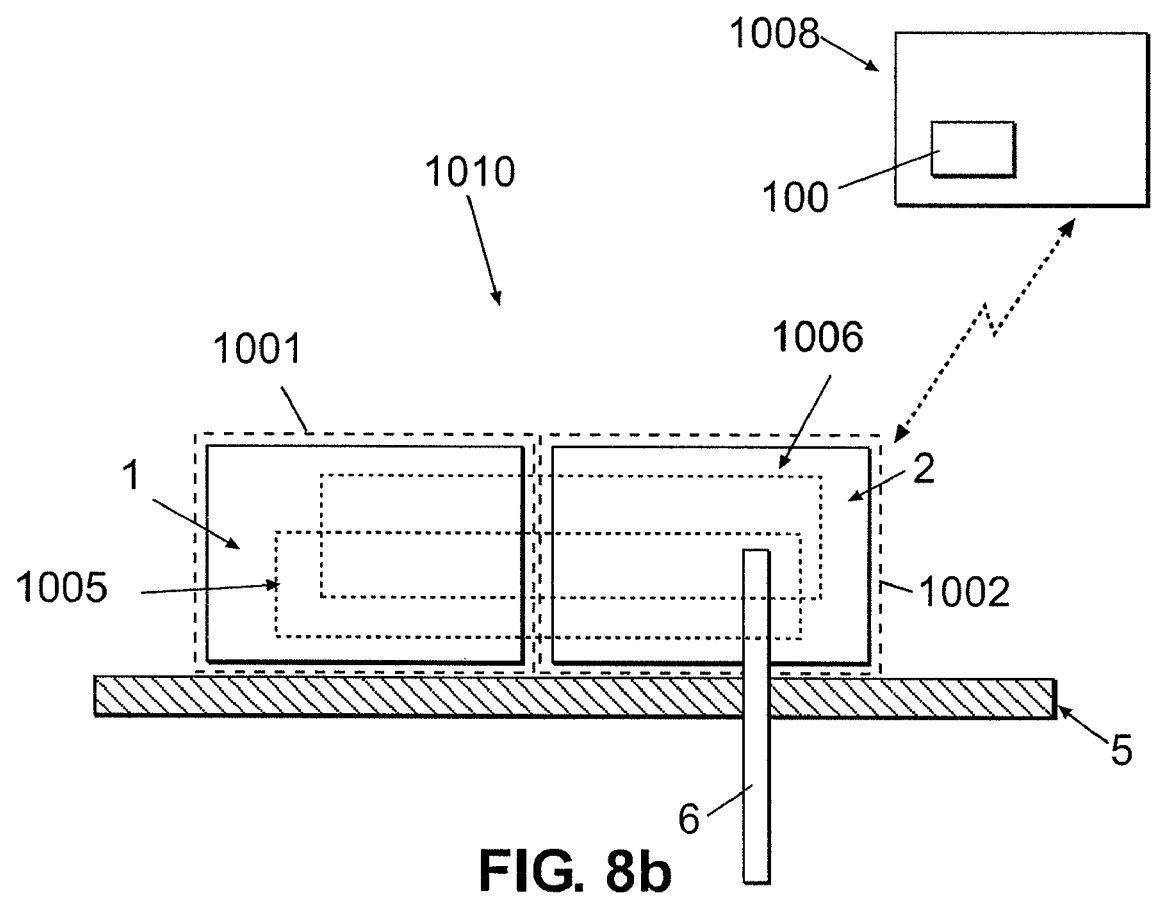

Referring to FIGS. 8a and 8b, schematic diagrams of exemplary embodiments of an insulin infusion system are shown. In the embodiments shown in FIGS. 8a and 8b, blood glucose readings, required for tailored basal insulin profile determination as performed, for example, by the tailored basal insulin profile mechanism 100, are received from a continuous subcutaneous glucose monitor 1006. A communication link between the continuous subcutaneous glucose monitor 1006 and the tailored basal insulin profile mechanism 100 residing, for example, in the remote control unit 1008, is maintained, thus enabling communication of programming instructions, data handling, and user inputs.

FIG. 8a depicts an infusion system in which the current blood glucose (BG) is measured by a continuous subcutaneous glucose monitor 1006 housed separately from the rest of the infusion system. FIG. 8b depicts an infusion system in which the continuous subcutaneous glucose sensing (monitoring) apparatus 1006 is located in the patch unit 1010 of the insulin delivery system (i.e., the sensing apparatus 1006 is housed in the patch unit 1010). Thus, in the embodiments shown in FIG. 8b, the insulin dispensing apparatus 1005 and glucose sensing apparatus 1006 constitute a single delivery device, and may therefore use a single cannula 6 to perform both the dispensing and sensing operation of the infusion system. Alternatively, in some embodiments, the sensing apparatus and the dispensing apparatus may have separate cannulae that penetrate the skin 5 and reside in the subcutaneous tissue. As further shown in FIG. 8b, the delivery (i.e., infusion) system may include two parts—a reusable part 1 and a disposable part 2, with each part respectively having a separate housing 1001, 1002.

Figure 9A:
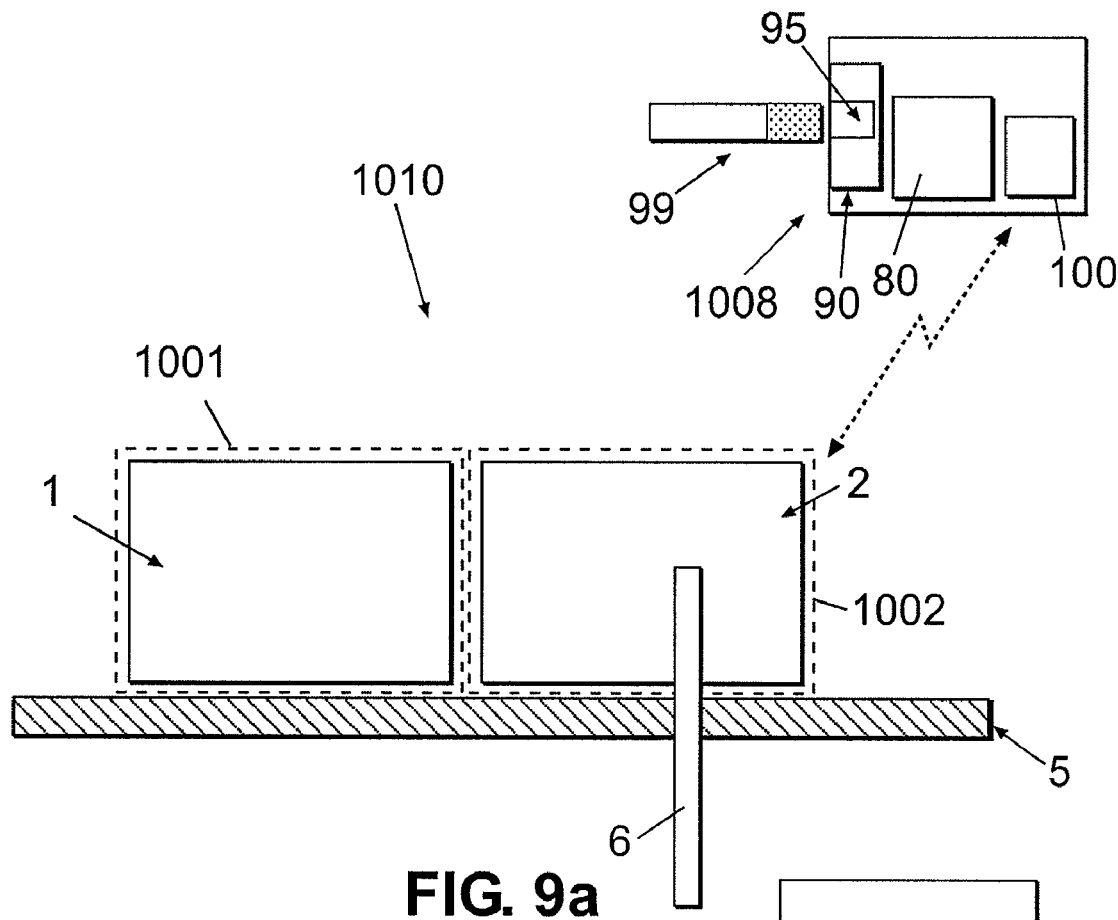

Referring to FIGS. 9a, b and c, schematic diagrams of three exemplary embodiments of the insulin dispensing systems, each including a glucometer 90 to be used to measure and determine blood glucose (BG) and provide the determined blood glucose as inputs for a tailored basal insulin profile mechanism 100 are shown. FIG. 9a depicts a glucometer 90 located in the remote control unit 1008 of the device. As shown, the glucometer 90 includes an opening 95 for receiving a test strip 99. The user may extract blood from the body, place the blood on the test strip 99 and insert the strip into the opening. The glucose readings 90, as measured and processed by the glucometer, are displayed on a screen 80 of the remote control unit 1008.

Figure 9B:
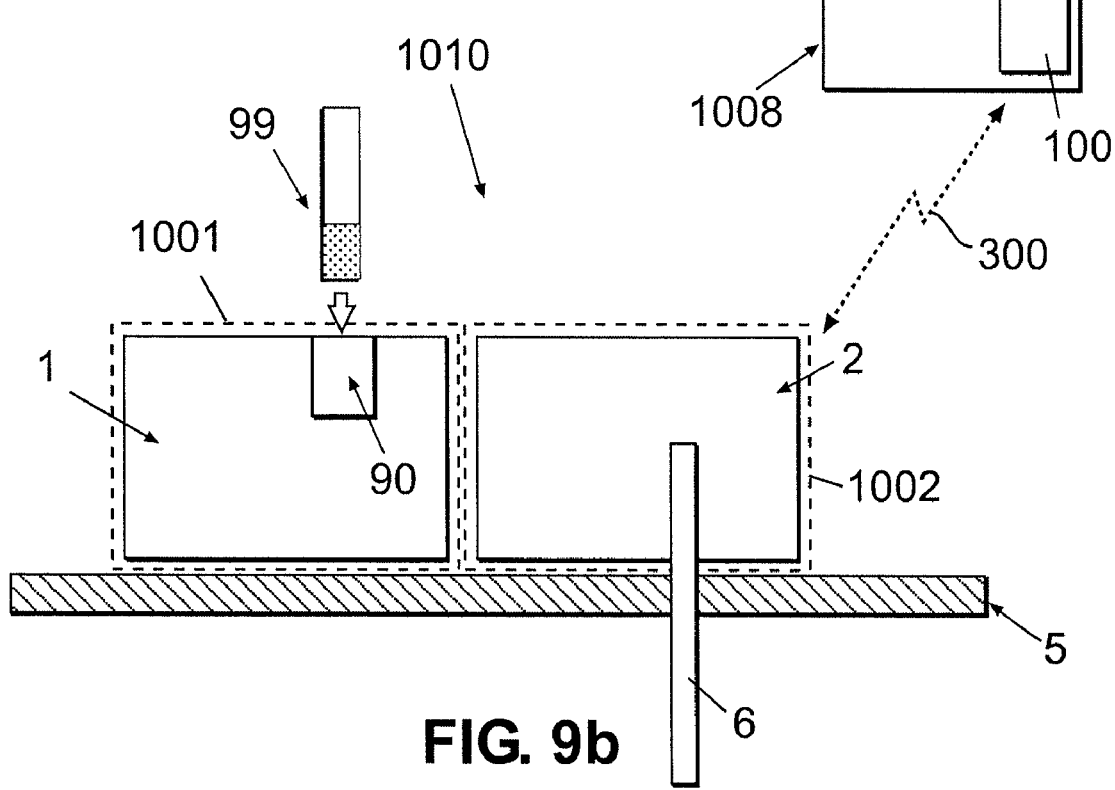

FIG. 9b depicts a glucometer 90 located in the reusable part 1 of the patch unit 1010. A communication channel 300 between the glucometer 90 residing in the patch unit 1010 and a tailored basal insulin profile mechanism 100 which may reside, for example, in the remote control unit 1008 is established and maintained, thus enabling communication of programming instructions/commands, acquired data and user inputs. As further shown in FIG. 9b, the glucometer 90 may include an opening to receive a test strip 99 on which a blood sample was deposited to enable the glucometer 90 to measure the blood glucose and generate signal representative of the blood glucose to thus enable determination of an infusion profile to control the infusion of insulin for the patient whose blood was sampled.

FIG. 9c depicts an exemplary embodiment of the insulin dispensing system in which glucose levels are determined by a glucometer housed separately from other units/modules of the dispensing system. The glucose level(s) thus determined may be provided to a remote control unit 1008 to enable determination and/or adjustment of the infusion profile to control infusion of insulin to the user's body.

Figure 10B:
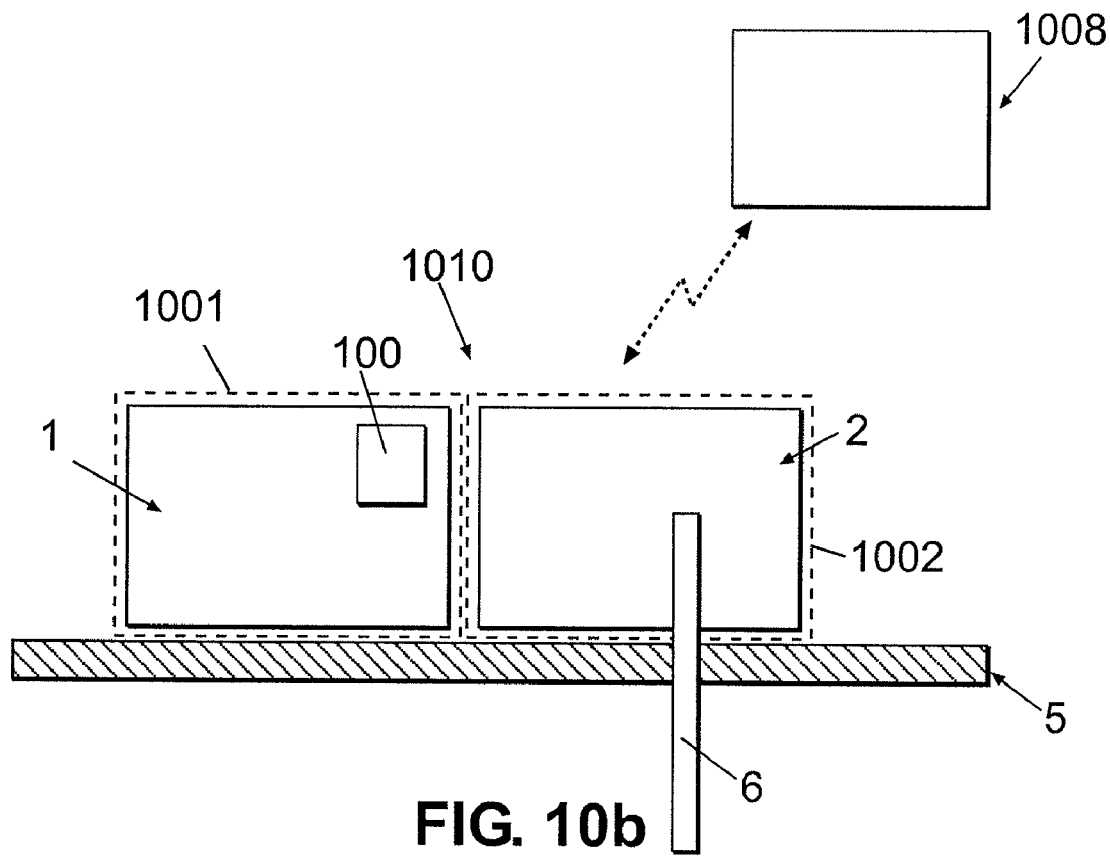

Referring to FIGS. 10a-b, schematic diagrams of two exemplary embodiments of insulin dispensing systems, each having a respective a tailored basal insulin profile mechanism in different respective locations are shown. In the embodiments shown, a patch unit 1010 includes two parts located in two housings 1001, 1002, namely, a reusable part 1 and a disposable part 2. The relatively inexpensive components of the patch unit generally reside in the disposable part 2 (e.g., cannula 6), while the relatively more expensive components reside in the reusable part 1. In some embodiments, the cannula can be attached to a skin-securable cradle part (together constituting the needle unit), thus enabling connection and disconnection of the patch unit from the needle unit.

The insulin dispensing system may also include a remote control unit 1008. Programming instructions/commands may be provided and communicated by the remote control via a user interface (e.g., buttons) located on the patch unit.

As shown in FIG. 10a, the tailored basal insulin profile apparatus 100 is located in the remote control unit 1008. In FIG. 10b, the tailored basal insulin profile mechanism (apparatus) 100 is located in the reusable part 1 of the patch unit 1010.

Figure 11:
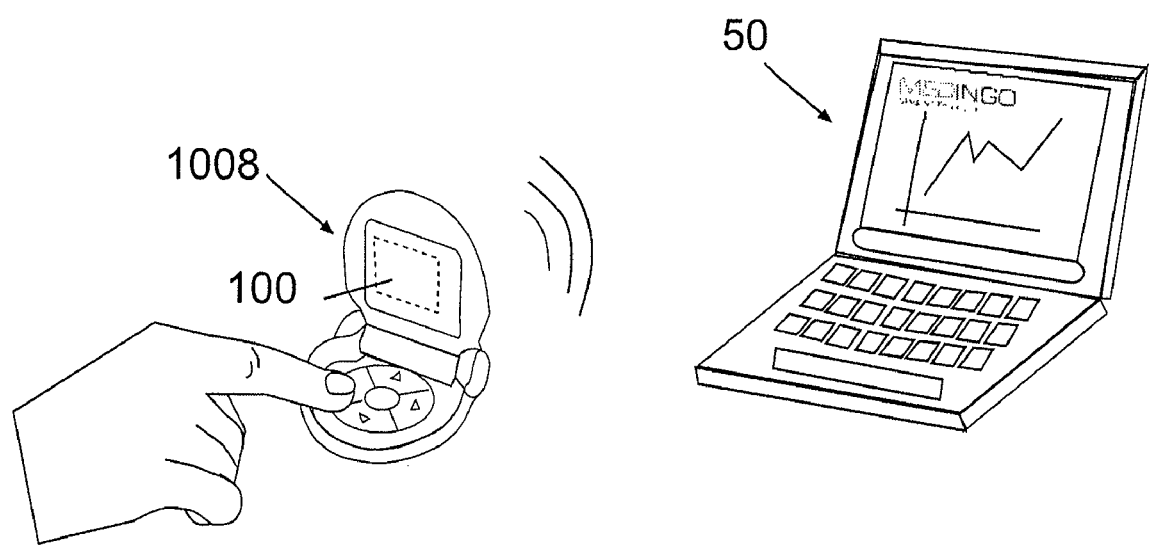
FIG. 11 is a perspective view of an exemplary embodiment of a system that includes a personal computer and a remote control unit having a tailored basal insulin profile mechanism.

Referring to FIG. 11, a perspective view of an exemplary embodiment of a system that includes a personal computer (PC) in communication with a remote control unit 1008 that includes a tailored basal insulin profile mechanism 100 is shown.

In some embodiments, any changes of the optimal basal profile determined or adjusted by the mechanism 100 may be saved (e.g., to the computer 50, or to any storage device anywhere on the dispensing system or a remote device) and/or may be displayed in any graphical or non-graphical manner. In some embodiments, saved data may automatically be sent to a user's practitioner (e.g. by electronic mail) for evaluation, validation or any other clinical intervention.

Accordingly, devices, systems and methods for implementing tailoring basal insulin delivery to a user are described herein. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. All of the foregoing patents, applications, and publications referenced in this specification are hereby incorporated by reference herein in their entireties. Other aspects, advantages, and modifications are considered to be within the scope of the following claims. The claims presented are representative of the inventions disclosed herein. Other, unclaimed inventions are also contemplated.

What is claimed is:

1. A system to deliver insulin to a user's body, the system comprising:
 a dispensing unit to deliver the insulin to the body; and
 a control mechanism to control delivery of basal insulin according to a predetermined basal infusion pattern specifying a sequence of basal rates for the user to receive at various time instances over a period of time, the control mechanism further configured to select, based on one or more personal characteristics of the user, the predetermined basal infusion pattern from a plurality of predetermined basal infusion patterns stored in a storage unit, the plurality of predetermined basal infusion patterns specifying respective sequences of basal rates for the user to receive at the various times instances over the period of time,
 wherein the control mechanism configured to select the predetermined basal infusion pattern is configured to:
  compute scores for at least some of the plurality of predetermined basal infusion patterns based on the one or more personal characteristics of the user, and
  select a pattern from the at least some of the plurality of the predetermined basal infusion patterns with a corresponding score determined to be a best score of the scores computed for the at least some of the plurality of the predetermined basal infusion patterns.

2. The system of claim 1 wherein the dispensing unit comprises:
 a reservoir to hold the insulin;
 a cannula having an end for placement within the user's body; and
 a pump to deliver the insulin from the reservoir to the cannula.

3. The system of claim 1 wherein the control mechanism to control delivery of the basal insulin comprises: a processor configured to control delivery of the basal insulin by the pump according to the selected basal infusion pattern, the basal infusion pattern comprising a pre-defined sequence of basal infusion rate changes.

4. The system of claim 3 wherein the rate changes of the pre-defined sequence are defined at intervals of one hour or shorter.

5. The system of claim 3 wherein the pre-defined sequence comprises a pre-defined sequence of deviations from an average basal infusion rate.

6. The system of claim 1 wherein the control mechanism is further configured to: time shift the basal infusion pattern based on the type of basal insulin to be held within a reservoir of the dispensing unit.

7. The system of claim 1 further comprising a user input interface in communication with the control mechanism, wherein the control mechanism is further configured to adjust the magnitude of the basal insulin delivered without disrupting the sequence of basal infusion rate changes defined by the basal infusion pattern in response to user input, entered through the user input interface, to increase or decrease the dosage of insulin delivered by the dispensing unit.

8. The system of claim 1 wherein the control mechanism comprises a basal infusion rate pattern mechanism to determine the basal infusion pattern based on the one or more personal characteristics of the user.

9. The system of claim 8 wherein the basal infusion pattern mechanism is configured to determine the basal infusion pattern based on the one or more personal characteristics of the user, including one or more of: age, body-mass index (BMI), bolus insulin requirements, sex, duration of diabetes, metabolic control, physical activity, sleep pattern, sleep duration, hemoglobin A1c values, age at manifestation of Diabetes Mellitus (DM), pyramidal insulin per kilogram, prandial insulin per day, total insulin per kilogram and total insulin per day.

10. The system of claim 8 wherein the basal infusion pattern mechanism configured to determine the basal infusion pattern is configured to: select a basal infusion pattern from a plurality of pre-defined patterns based on the one or more personal characteristics of the user.

11. The system of claim 1 wherein the basal infusion pattern is selected based on the user's age.

12. The system of claim 1 wherein the selected basal infusion pattern is determined based on physiological diurnal needs of basal insulin.

13. The system of claim 1 wherein the plurality of predetermined basal infusion patterns includes a biphasic pattern having a peak at a point of the pattern corresponding to a period of early morning and a peak at another point of the pattern corresponding to a period of late afternoon.

14. The system of claim 1 wherein the plurality of predetermined basal infusion patterns includes a monophonic pattern having a broad insulin peak at a point of the pattern corresponding to a period of around noon.

15. The system of claim 1 wherein the system is further configured to:
 collect data regarding efficacy of the selected basal infusion pattern; and
 adjust the selected basal infusion pattern based on the collected data.

16. The system of claim 1 wherein the control mechanism to control delivery of the basal insulin according to the selected basal infusion pattern is configured to:
 determine the basal infusion pattern based on the one or more personal characteristics of the user; and
 perform an evaluation of suitability of the determined basal infusion pattern based on glycemic status of the user.

17. The system of claim 16 wherein the control mechanism configured to perform the evaluation of the suitability of the determined basal infusion pattern is configured to: evaluate the suitability of the determined basal pattern based on data representative of deviations of a user's glucose level from a target zone.

18. The system of claim 16 wherein the control mechanism configured to perform the evaluation of the suitability of the determined basal infusion pattern is configured to: evaluate the suitability of the determined basal pattern based on data representative of a user's hemoglobin A1C levels.

19. The system of claim 16 wherein the control mechanism is further configured to: adjust the selected basal infusion pattern based on the evaluation indicating lack of suitability of the determined basal infusion pattern.

20. The system of claim 16 wherein the control mechanism is further configured to: determine another basal infusion pattern based on the evaluation indicating lack of suitability of the basal infusion pattern.

21. The system of claim 20 wherein the control mechanism configured to determine the other basal infusion pattern based on the evaluation indicating lack of suitability is configured to: select the other basal infusion pattern from the plurality of basal infusion patterns based on the evaluation indicating lack of suitability.

22. The system of claim 1 further comprising: a remote control housed remotely from the dispensing unit.

23. The system of claim 1 further comprising: a glucometer to measure blood glucose levels of the user.

24. The system of claim 23 wherein the control mechanism to control delivery of the basal insulin according to the selected basal infusion pattern further configured to: control delivery of the basal insulin based, at least in part, on the measured blood glucose levels of the user.

25. The system of claim 1 further comprising: a cradle unit securable to the body of the user, the cradle unit configured to receive at least the dispensing unit.

26. An apparatus to deliver doses of basal insulin to a body of a user, the apparatus comprising:
a user interface to receive input regarding at least one characteristic of the user; and
a tailored basal insulin profile mechanism to select a basal infusion pattern for the user specifying a sequence of basal rates for the user to receive at various time instances over a period of time from a plurality of pre-determined basal insulin infusion patterns stored in a storage unit based, at least in part, on the received input regarding the at least one characteristic of the user, the plurality of predetermined basal infusion patterns specifying respective sequences of basal rates for the user to receive at the various times instances over the period of time,
wherein the tailored basal insulin profile mechanism to select the predetermined basal infusion pattern is configured to:
compute scores for at least some of the plurality of predetermined basal infusion patterns based on the one or more personal characteristics of the user, and
select a pattern from the at least some of the plurality of the predetermined basal infusion patterns with a corresponding score determined to be a best score of the scores computed for the at least some of the plurality of the predetermined basal infusion patterns.

27. The apparatus of claim 26 further comprising: a dispensing unit to deliver the basal insulin to the user's body according to the selected basal infusion pattern.

28. The apparatus of claim 26 wherein the selected basal infusion pattern includes a pre-defined sequence of basal infusion rate changes for delivery of the basal insulin to the user's body.

29. The apparatus of claim 28 wherein the rate changes of the selected basal infusion pattern are defined at intervals of one hour or shorter.

30. The apparatus of claim 28 wherein the pre-defined sequence of basal infusion rates includes a pre-defined sequence of deviations from an average basal infusion rate.

31. The apparatus of claim 26 wherein the tailored basal insulin profile mechanism is further configured to time shift the selected pattern based on the type of basal insulin to be used.

32. The apparatus of claim 26 wherein the tailored basal insulin profile mechanism configured to select the basal infusion pattern based on the input regarding the at least one characteristic of the user is configured to select the basal infusion pattern based on one or more of: age, body-mass index (BMI), bolus insulin requirements, sex, duration of diabetes, metabolic control, physical activity, sleep pattern, sleep duration, hemoglobin A1c values, age at manifestation of Diabetes Mellitus (DM), pyramidal insulin per kilogram, prandial insulin per day, total insulin per kilogram and total insulin per day.

33. The apparatus of claim 26 wherein the tailored basal insulin profile mechanism configured to select the basal infusion pattern is configured to select the basal insulin infusion pattern based on the user's age.

34. The apparatus of claim 26 wherein the tailored basal insulin profile mechanism is further configured to: perform an evaluation of suitability of the selected basal infusion pattern based on glycemic status of the user.

35. The apparatus of claim 34 wherein the tailored basal insulin profile mechanism configured to perform the evaluation of the suitability of the determined basal infusion pattern is configured to: evaluate the suitability of the selected basal pattern based on data representative of deviations of a user's glucose level from a target zone.

36. The apparatus of claim 34 wherein the tailored basal insulin profile mechanism configured to perform the evaluation of the suitability of the selected predetermined basal infusion pattern is configured to: evaluate the suitability of the selected basal pattern based on data representative of a user's hemoglobin A1C levels.

37. The apparatus of claim 34 wherein the tailored basal insulin profile mechanism is further configured to: adjust the selected basal infusion pattern based on the evaluation indicating lack of suitability of the determined basal infusion pattern.

38. The apparatus of claim 34 wherein the tailored basal insulin profile mechanism is further configured to: select another basal infusion pattern based on the evaluation indicating lack of suitability of the basal infusion pattern.

39. The system of claim 1 wherein the period of time comprises a 24 hour period of time.

* * * * *